(12) United States Patent
Hargis et al.

(10) Patent No.: US 8,367,058 B2
(45) Date of Patent: Feb. 5, 2013

(54) METHOD FOR BACTERIOPHAGE DELIVERY AND AMPLIFICATION

(75) Inventors: Billy M. Hargis, Fayetteville, AR (US); Stacy E. Higgins, Fayetteville, AR (US); Lisa Bielke, Fayetteville, AR (US); Guillermo L. Tellez, Fayetteville, AR (US); Lisa A. Newberry, Benton, AR (US); Gerardo Nava, Urbana, IL (US); Ann M. Donoghue, Springdale, AR (US); Daniel J. Donoghue, Springdale, AR (US)

(73) Assignees: The United States of America, as Represented by the Secretary of Agriculture, Washington, DC (US); The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 13/091,762

(22) Filed: Apr. 21, 2011

(65) Prior Publication Data

US 2011/0200561 A1    Aug. 18, 2011

Related U.S. Application Data

(60) Division of application No. 11/473,449, filed on Jun. 23, 2006, now Pat. No. 7,951,579, which is a continuation-in-part of application No. 10/818,273, filed on Apr. 5, 2004, now abandoned.

(60) Provisional application No. 60/461,042, filed on Apr. 7, 2003.

(51) Int. Cl.
  *A01N 63/00* (2006.01)
(52) U.S. Cl. ..................................... 424/93.6
(58) Field of Classification Search .......... None
  See application file for complete search history.

(56) References Cited

U.S. PATENT DOCUMENTS

| | | | |
|---|---|---|---|
| 6,485,902 B2 | 11/2002 | Waddell et al. | |
| 2003/0032036 A1 | 2/2003 | Agrawal et al. | |
| 2004/0219519 A1 | 11/2004 | Hargis et al. | |
| 2004/0223954 A1 | 11/2004 | Bruessow et al. | |
| 2007/0154459 A1 | 7/2007 | Hargis et al. | |

FOREIGN PATENT DOCUMENTS

| WO | WO 01/50866 | 7/2001 |
|---|---|---|
| WO | WO 02/07742 | 1/2002 |

OTHER PUBLICATIONS

Remington's (Remington's Pharmaceutical Sciences, 17th ed., Mack Publishing Company, 1985, p. 371).*
Bielke, L. et al., "*Salmonella* host range of bacteriophage that infect multiple genera," Poultry Sci. (2007) 86:2536-2540.
Carlton, R., "Phage therapy: past history and future prospects," Archivum immunologiae et Therapiae Experimentalis (1999) 47:267-274.
Goodridge, L. et al., "Bacteriophage biocontrol and bioprocessing: application of phage therapy to industry," SIM News (2003) 53(6):254-262.
Higgins, J.P. et al., "Use of a specific bacteriophage treatment to reduce *Salmonella* in poultry products," Sci. (2005) 84:1141-1145.
Huff, W., et al., "Prevention of *Escherichia coli* respiratory infection in broiler chicken with a bacteriophage aerosol spray," Poultry Sci. (2002) 81:1486-1491.
Huff, W.E., et al., "Bacteriophage treatment of a severe *Escherichia coli* respiratory infection in broiler chickens," Avian Diseases (2003) 47:1399-1405.
Jensen, E.C. et al., "Prevalence of broad-host-range lytic bacteriophage of *Sphaerotilus natans, Escherichia coli,* and *Pseudomonas aeruginosa*," App. Envirn. Microbiol. (1998) 64(2):575-580.
Joerger, R.D., "Alternatives to antibiotics: bacteriocins, antimicrobial peptides and bacteriophages," Poultry Sci. (2003) 82:640-647.
Madie, P., "*Salmonella* and *Campylobacter* infections in poultry," Proc. Solvay Chicken Health Course. Grunner U. Peterson Massey University, Palmerston North, New Zealand, pp. 69-82 (1992).
Miller, F., "Biological warfare. Get the bacteria before they get you," Arkansas Land and Life (2002) 7(2):14-15.
Park, S., et al., "Isolation of bacteriophages specific to a fish pathogen, *Pseudomonas plecoglossicida*, as a candidate for disease control," Applied Environmental Microbiology (2002) 66(4):1416-1422.
Slopek, B., et al., "Results of bacteriophage treatments of suppurative bacterial infections in the Years 1981-1986," Arch Immunol. Ther. Exp. (1987) 35:569-583.
Slopek, S., et al,, "Results of bacteriophage treatment of suppurative bacterial infections III. Detailed evaluation of the results obtained in further 150 cases," Archivum Immunologiae et Therepiae Experimentalis (1984) 32:317-335.
Smith, H., et al., "Effectiveness of phages in treating experimental *Escherichia coli* diarrhoea in calves, piglets and lambs," Journal of General Microbiology (1983) 129;2659-2675.
Smith, H., et al., "Successful treatment of experimental *Escherichia coli* infections in mice using phage: Its general superiority over antibiotics," Journal of General Microbiology (1982)128:307-318.
Vugia, D., et al., "FoodNet. Preliminary FoodNet data on the incidence of foodborne illnesses—selected sites, United States, 2001," Morbidity and Mortality Weekly Report (2002) 51(15):325-329.
United States Office Action for U.S. Appl. No. 10/818,273 dated Apr. 23, 2007 (12 pages).
United States Office Action for U.S. Appl. No. 11/473,449 dated Oct. 28, 2008 (10 pages).
United States Office Action for U.S. Appl. No. 11/473,449 dated Jun. 12, 2009 (9 pages).
United States Office Action for U.S. Appl. No. 11/473,449 dated Dec. 23, 2009 (7 pages).
United States Office Action for U.S. Appl. No. 11/473,449 dated Jul. 1, 2010 (5 pages).

* cited by examiner

*Primary Examiner* — Brian J Gangle
(74) *Attorney, Agent, or Firm* — Andrus, Sceales, Starke & Sawall, LLP

(57) ABSTRACT

Disclosed are methods of selecting wide host range bacteriophage capable of growing in a plurality of bacteria including pathogenic and non-pathogenic bacteria and bacteriophage selected by the methods. Also disclosed are methods of treating a subject infected with a pathogenic bacterium using bacteriophage and methods of decontaminating objects using bacteriophage. Also disclosed are methods of producing vaccines. In another aspect, methods of determining bacterial viability and methods of improving the sensitivity of a biosensor using wide host range bacteriophages are disclosed.

18 Claims, 8 Drawing Sheets

METHOD FOR BACTERIOPHAGE DELIVERY AND AMPLIFICATION

CROSS REFERENCE TO RELATED APPLICATION

This application is a divisional of U.S. patent application Ser. No. 11/473,449, filed Jun. 23, 2006, and published as U.S. Patent Publication No. 2007/0154459 on Jul. 5, 2007, which application is a continuation-in-part of U.S. application Ser. No. 10/818,273, filed Apr. 5, 2004 and claims the benefit of that application and U.S. Provisional Application No. 60/461,042 filed Apr. 7, 2003, which are incorporated herein by reference.

STATEMENT REGARDING FEDERALLY SPONSORED RESEARCH OR DEVELOPMENT

This invention was made with Government support under the terms of Grant No. 2001-34211-10288 awarded by the United States Department of Agriculture, Cooperative State Research Education and Extension Service. The Government has certain rights in the invention.

BACKGROUND

Foodborne illness affects more than 76 million Americans each year with an estimated cost of 1.4 billion dollars in lost human productivity, medical expenses and increased animal production costs in the United States alone (FoodNet, 2002; Madie, 1992). Salmonellosis contributes 36% of this incidence. With the increased resistance of bacteria to anti-microbials and the withdrawal of antibiotics, such as the fluoroquinolones, from use in poultry production by the Food and Drug Administration, effective alternative treatments for prevention and treatment of bacterial diseases must be developed. Strain-specific bacteriophage therapy has been suggested as an alternative to antimicrobials for the control of bacterial diseases, such as Salmonellosis, in animals and man (Slopek et al., 1987; Smith and Huggins, 1982, 1983; Park et al., 2000, Huff et al., 2001).

Bacteriophages are members of a specific group of viruses that only infect and replicate in bacteria, and have no potential to infect animals or plants. Replication of the bacteriophage can result in lysis and death of the host bacterial cells. Bacteriophages are ubiquitous and can be found in water, sewage or soil. Bacteriophages are characterized as extremely host specific and will often infect and replicate in only one bacterial species or only a single serotype within a species. This specificity of the bacteriophage for a particular host bacterium has been utilized in classifying bacteria, but has been a limiting factor in using bacteriophage to kill bacteria and treat or prevent the spread of bacterial diseases. There have been numerous attempts, with some success, to use bacteriophages to treat bacterial infections (Slopek et al., 1987; Smith and Huggins, 1982, 1983; Park et al., 2000, Huff et al., 2001). However, commercial use of bacteriophages for treatment of infections has not gained widespread acceptance in part due to the need to identify an effective and strain-specific bacteriophage for each disease outbreak.

The use of bacteriophages for therapy or decontamination purposes has been limited for several reasons, including strain specificity of some bacteriophage. Strain specificity requires that the bacteria are identified and the susceptibility of the bacteria to the bacteriophage assessed before using the bacteriophage. This process is time-consuming and costly. Additionally, bacteriophages require bacteria for growth and thus it is often difficult to ensure removal of the bacteria from the bacteriophage preparation. This is especially problematic if the bacteriophage only grows in pathogenic bacteria. In addition, it has proved difficult to deliver large numbers of bacteriophages to the sites of infection. For example, bacteriophages are lost as they travel through the upper gastrointestinal tract, which has uniformly resulted in the need for administration of large numbers of bacteriophages for the treatment of enteric infection. Thus, bacteriophage therapy while promising has not proved useful due to these limitations.

SUMMARY

Methods of selecting a wide host range bacteriophage by isolating a bacteriophage capable of lysing a plurality of bacteria are provided. The plurality of bacteria suitably includes both pathogenic and non-pathogenic bacteria. Methods of selecting a bacteriophage capable of surviving passage through the gastrointestinal tract of a subject are also provided. Wide host range bacteriophages selected according to the methods are also disclosed.

In another aspect, medicaments for treating infections caused by pathogenic bacteria are disclosed. The medicament includes a wide host range bacteriophage infected non-pathogenic bacterium, wherein the bacteriophage is selected according to the disclosed methods.

In yet another aspect, methods of treating a subject infected with a bacterium are disclosed. The subject is treated by administering a wide host range bacteriophage selected by the disclosed methods to the subject. The bacteriophage lyses the bacterium to treat the infection.

In a further aspect, methods of decontaminating an object by applying a wide host range bacteriophage to the object are provided. The object is decontaminated by the bacteriophage lysing bacteria contaminating the object.

In a still further aspect, methods of producing vaccines are disclosed. Bacteria are infected with a bacteriophage selected according to the disclosed methods and lyse the bacteria to produce a killed bacterial vaccine.

In another aspect, methods of determining bacterial viability in a sample are disclosed. Bacteriophages capable of lysing the bacteria are added to a sample containing the bacteria and bacteriophage reproduction in the sample is indicative of the viability of the bacteria in the sample.

In a further aspect, methods of improving the sensitivity of a biodetector are disclosed. A sample suspected of containing bacteria is treated with the bacteriophage selected according to the disclosed methods. Lysis of the bacteria in the sample and reproduction of the bacteriophage are indicative of live bacteria in the sample.

DETAILED DESCRIPTION

Figure 1:
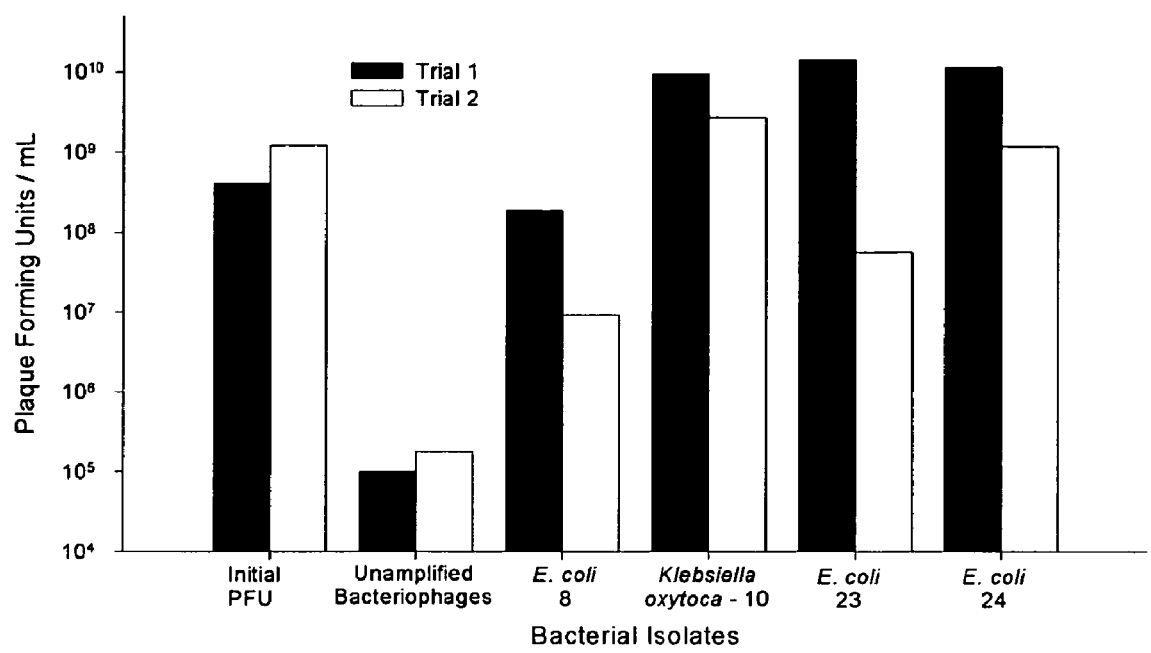
FIG. 1 is a graph showing amplification of *Salmonella enteritidis*-selected bacteriophages in alternative host bacteria. The combined bacteriophages were amplified in alternative host bacteria (*E. coli*-3 isolates, *Klebsiella* sp.-1 isolate) for four rounds of infection. The plaque forming units (PFU) from the final round were determined in *Salmonella enteritidis* using soft agar overlay plates.

Commercial and therapeutic applications using bacteriophage to reduce bacterial load have not been developed for several reasons, including strain specificity of the bacteriophage, difficulty of delivery and fear of bacterial contamination of bacteriophage preparations. A method of selecting bacteriophage capable of growing in a wide host range bacterium is disclosed. The method involves isolation of bacteriophage capable of lysing a plurality of bacteria. The ability of a bacteriophage to lyse a bacterium indicates that the bacteriophage is capable of growing or amplifying its genome within a particular bacterium. Isolation of a bacteriophage means that the bacteriophage has been separated from its original source and is capable of amplification outside its original source. Interestingly, the isolated bacteriophage need not necessarily be purified separate from other bacteriophage for this method to work.

This method produced a surprising number of wild-type bacteriophage isolates that can be readily propagated in non-related or only distantly related bacteria. The bacteria useful in the methods may be different strains of the same species or may be different species. The bacteria may be from different genera. As described in the Examples below, a variety of wide host range bacteriophages were isolated from a municipal wastewater treatment plant and were initially isolated due to their ability to amplify on *Salmonella enteritidis*. Bacteriophages may also be isolated from a variety of sources including, but not limited to, lakes, rivers, ponds, livestock farms, food processing facilities, soil, manure, hospitals, nursing homes, residences, schools, restaurants, daycare centers, toys, food products, and animals or their carcasses, including humans, domestic and undomesticated animals, poultry, fish, and their by-products. Several of the isolated bacteriophages were capable of lysing other species of *Salmonella*, including pathogenic and non-pathogenic strains, as well as *Escherichia coli* and *Klebsiella oxytoca*.

This method may be used to select bacteriophages that target and kill a specific bacterial pathogen, and then to identify non-pathogenic bacteria or beneficial microflora that can serve as an alternative host for in vitro propagation of the bacteriophage. The bacteriophage may be selected for growth in a wide variety of bacterial genera, including, but not limited to, *Salmonella, Escherichia, Porphyromonas, Prevotella, Fusobacterium, Campylobacter, Streptococcus, Staphylococcus, Listeria, Klebsiella, Bacillus, Citrobacter, Enterobacter, Enterococcus, Bifidobacterium, Leuconostoc, Proteus, Kluyvera, Lactobacillus,* and *Pediococcus.* Representative bacterial species for use in the method include, but are not limited to, *Staphylococcus xylosus, Klebsiella oxytoca, Klebsiella travesanii, Citrobacter freundii, Enterobacter cloacae, Enterococcus faecium, Kluyvera ascorbata, Lactobacillus casei, Lactobacillus cellobiosus, Lactobacillus fermentum, Lactobacillus helveticus, Lactobacillus paracasei, Lactobacillus salivarius, Pediococcus parvulus, Salmonella enteritidis, Salmonella heidelberg, Salmonella montevideo, Salmonella ohio, Salmonella typhimurium, Salmonella agona, Salmonella infantis, Salmonella minnesota, Listeria monocytogenes, Staphylococcus aureus, Enterococcus faecium, Porphyromonas gingivalis, Prevotella intermedia, Fusobacterium nucleatum, Campylobacter rectus* and *Escherichia coli.*

Another obstacle in the treatment of bacterial infections with bacteriophages is the tremendous reduction of viable bacteriophages as they pass through the relatively low pH conditions of the upper gastrointestinal tract. Initial success in using bacteriophage therapy for treating enteric Salmonellosis has only previously been achieved with simultaneous administration of very large numbers of bacteriophages with a buffering solution. To overcome this obstacle, the bacteriophage may be further selected to survive adverse conditions including, but not limited to, low pH (such as a pH of 2.0 or 4.0), high pH (such as pH 10.0), desiccation, freezing, high temperature, low temperature, and high or low pressure. One of ordinary skill in the art could select for bacteriophage capable of surviving passage through the gastrointestinal tract in a variety of ways including, but not limited to, growth in successively lower pH environments. The bacteriophage may also be selected to survive passage through the gastrointestinal tract of a subject. The bacteriophage is isolated from the subject after passage through the gastrointestinal tract of the subject. The resulting selected bacteriophage is more capable of surviving the gastrointestinal tract of a subject.

An alternative method of selecting a bacteriophage capable of surviving passage through the gastrointestinal tract of a subject includes infecting non-pathogenic bacteria with bacteriophage to produce bacteriophage infected non-pathogenic bacteria and administering the bacteriophage infected non-pathogenic bacteria to the subject. It is believed that the bacteriophage pass through the upper digestive tract encased in the non-pathogenic bacteria. It is further believed that, once in the lower digestive tract, a portion of the bacteriophages will lyse the non-pathogenic bacteria, enter the lower digestive tract and be available to attack pathogenic bacteria in the lower digestive tract.

The identified wide host range bacteriophage are useful in commercial and therapeutic applications. A combination of the selected wide host range bacteriophage may be utilized to allow for overlapping bacterial specificity. In other words, bacteriophage may be combined such that the combination will kill a wide array of bacterial species. This feature may allow use of the bacteriophage to kill bacteria without a need for prior susceptibility testing or bacterial strain typing prior to administration of the bacteriophage. Such testing is cost and time intensive and represents another reason bacteriophage therapy has not gained widespread use to date.

Amplification of bacteriophage for use in treatment of animal or human infections, or treatment of products intended for use in food or feed, has traditionally carried some risk of accidental infection with the target pathogenic bacterium if separation of bacteriophage from host pathogenic bacteria is not complete. The ability to amplify bacteriophage in alternative non-pathogenic hosts greatly reduces this potential threat, and also reduces the costs associated with redundant steps to ensure exclusion of the amplification host from the bacteriophage product. By amplification of prophylactic or therapeutic bacteriophage in non-pathogenic hosts during manufacture, risk of introduction of pathogenic bacteria is eliminated. Similarly, alternative hosts which produce little or no endotoxins or exotoxins can be selected for amplification of therapeutic bacteriophage under commercial conditions, thereby reducing or eliminating the need for purification (removal of toxins) for use of such preparations on food, and feed, or in animals and humans.

The resulting bacteriophage infected non-pathogenic bacteria may be used to prepare a medicament and the medicament may be used to treat an infection caused by a pathogenic bacterium in an infected subject. Suitable medicament and methods of treating subjects infected with a bacterium are provided. The medicament may be administered by any method known to those of skill in the art, including but not limited to, injection (such as intravenous, intramuscular and intraperitoneal), ingestion (such as in food, water, tablets, capsules or by gavage), topical application (in a wash, spray, cream, toothpaste, toothbrush, or mouth rinse or the like), or aerosolization (such as in a mist, fog or propellant-based delivery device).

The medicament may contain one or more bacteriophage alone or in combination with non-pathogenic bacteria. The medicament may be used to treat a subject infected with a bacterium, wherein the bacteriophage lyse the bacteria to treat the infection. The subject may be a domestic animal, a poultry, a fish or a human. Domestic animals include, but are not limited to, a cow, a pig, a rabbit, a sheep, a goat, a horse, a hamster, a dog, a cat, a mouse, and a rat. Poultry include, but are not limited to, a chicken, a turkey, a guinea, a quail, a duck, a goose, a pheasant, a partridge, a grouse, a pigeon, a squab, an ostrich, an emu, and a rhea. Fish include, but are not limited to, a fresh finfish, a saltwater finfish, a crustacean, a mollusk, an alligator, a frog, an aquatic turtle, a jellyfish, a sea cucumber, a sea urchin, the roe of those animals, a catfish, and a tilapia.

The medicament and method of treatment may include treatment of infections including, but not limited to, enteric infections, skin infections, blood infections, respiratory infections, and gingival infections. The infection may be caused by any bacterium. Bacteria may suitably be selected from the group consisting of *Salmonella, Escherichia, Porphyromonas, Prevotella, Fusobacterium, Campylobacter, Streptococcus, Staphylococcus, Listeria, Klebsiella, Bacillus, Citrobacter, Enterobacter, Enterococcus, Bifidobacterium, Leuconostoc, Proteus, Kluyvera, Lactobacillus*, and *Pediococcus* species.

Methods of decontaminating an object comprising applying a wide host range bacteriophage to the object are also provided. Application of the bacteriophage to the object results in infection and lysis of contaminating bacteria by the bacteriophage. The bacteriophage may be a plurality of bacteriophages. The bacteriophage for use in the methods may comprise bacteriophage infected non-pathogenic bacteria or may have been prepared by amplification or passage in non-pathogenic bacteria.

One of skill in the art will appreciate that the bacteriophage may be applied to the object in a variety of ways which allow the bacteriophage to contact and infect the bacteria. Methods of applying bacteriophage to an object include, but are not limited to, applying an aqueous solution comprising the bacteriophage to the object. The aqueous solution may be applied by any means known to those of skill in the art including, but not limited to spraying, washing or submerging the object with the aqueous solution. The aqueous solution may comprise a liquid soap, or be carried by a pre-moistened wipe.

The object to be treated may be any object that may be contaminated with bacteria. Suitable objects for use in the methods include, but are not limited to, food products, plants, surfaces (such as those in buildings including restaurants, residences, nursing homes, kitchen countertops, hospitals and children's toys), animals, animal carcasses, and animal habitats. Food products include, but are not limited to fruits, vegetables, meat products, poultry products, seafood products, dairy products, raw food products and ready-to-eat food products. Surfaces include, but are not limited to, tables, floors, chairs, beds, toilets, showers and baths. Animals include, but are not limited to, domestic or undomesticated animals, fish, poultry and humans. Animal carcasses include, but are not limited to carcasses of domestic animals, poultry and fish. In the Examples below, wide host range bacteriophages were demonstrated to reduce bacterial contamination of both chicken and turkey carcasses when the bacteriophage were applied by spraying or rinsing the carcass with a solution comprising a wide host range bacteriophage.

Methods of producing vaccines are also disclosed. A bacterium useful in a vaccine preparation may be infected with a wide host range bacteriophage selected according to the disclosed methods to produce a killed bacterial vaccine. This method could be used to produce a killed bacterial vaccine specific for any bacterial pathogens. Bacterial pathogens include, but are not limited to *Salmonella, Escherichia, Staphylococcus, Streptococcus, Proteus*, and *Enterococcus*.

Methods of determining bacterial viability in a sample using the selected bacteriophages are also provided. Bacteriophage capable of lysing the bacteria in the sample may be added to the sample and amplification or growth of the bacteriophage is indicative of viable bacteria in the sample within the host range of the bacteriophage. The amplification or growth of the bacteriophage may be detected in a variety of ways as will be readily appreciated by those of skill in the art. Bacteriophage reproduction may be detected by methods including, but not limited to, subsequent plating on permissive bacteria to determine an increase in PFU, detection of expression of bacteriophage polypeptides, detection of expression of a bacteriophage controlled or carried marker, and detection of altered expression of a bacterial polynucleotide or polypeptide in response to infection with the bacteriophage. Markers are known to those of skill in the art and include fluorescent markers such as the green fluorescent protein (GFP), enzymatic markers such as β-galactosidase or alkaline phosphatase as well as others. The selected bacteriophages may also be used in biodetectors to provide information not only on the viability of bacteria, but also the identity of the bacteria. Briefly, a sample suspected of containing bacteria may be treated with a wide host range bacteriophage known to infect a specific set of bacteria. Growth or amplification of the bacteriophage is indicative of the viability of the bacteria in the sample and the identity of the bacteria in the sample.

The disclosed methods provide: 1) new approaches for selection and application of bacteriophages, and 2) novel approaches for selection and use of alternative hosts for the bacteriophages. These combined approaches provide powerful and cost-effective tools to prevent or treat infectious bacterial diseases, including enteric diseases. These approaches also have commercial use in biodetection systems. The following examples are meant to be illustrative only and are not intended as a limitation on the concepts and principles of the invention.

EXAMPLES

Bacteriophage Isolation.

Wastewater samples were obtained from a local municipal wastewater treatment plant and filtered through a 0.2 μM filter (Becton Dickinson, Sparks, Md.). A combination of 100 μL of $10^7$ CFU/mL *Salmonella enteritidis* PT 13A (SE) and 1 mL of the wastewater sample filtrate was added to 1.5 mL of tryptic soy agar (TSA; Pall-Gelman Laboratory, Ann Arbor, Mich.) and poured over a warm TSA petri plate. Plates were incubated overnight at 37° C., and those with confluent lysis of SE were then flooded with 15 mL of sterile 0.9% NaCl (saline). The fluid was then poured off the plate and filtered through a 0.2 μm filter. Serial ten-fold dilutions were made in saline. Plates were poured as described above with 1 mL of each bacteriophage dilution. Individual distinct plaques resulting from this plating were then differentiated on the basis of plaque morphology, and different plaques were sequentially passed on TSA plates at least three subsequent times to establish bacteriophage isolate purity.

With this technique, 44 bacteriophages were isolated from four wastewater samples collected on separate days. While several different plaque morphologies were noted and isolates were obtained from four different wastewater collections, no attempt to differentiate bacteriophages based on molecular or physiological characteristics was made.

Amplification of Bacteriophages in Non-Pathogenic Bacteria.

Thirty-five non-pathogenic enteric bacterial isolates were used to screen the 44-pooled bacteriophages for their ability to amplify in more than one species of bacteria. Non-pathogenic bacteria used in the screening process included *Bacillus* spp., *Staphylococcus xylosus*, *Staphylococcus* spp., *E. coli* (10 different enteric isolates), *Klebsiella oxytoca* (2 isolates), *Klebsiella travesanii*, *Citrobacter freundii* (6 isolates), *Enterobacter cloacae* (2 isolates), *Enterococcus faecium*, *Proteus* spp., *Kluyvera ascorbata*, *Lactobacillus casei* (2 isolates), *Lactobacillus cellobiosus*, *Lactobacillus fermentum*, *Lactobacillus helveticus*, *Lactobacillus paracasei*, *Lactobacillus salivarius*, *Pediococcus parvulus*. The pooled bacteriophages were combined with each individual bacterial isolate at a ratio of 1 mL bacteriophages, 3 mL bacterial culture (turbid culture), and 5 mL tryptic soy broth (TSB). This combination was incubated for 2 h at 37° C. The culture was then sterile filtered using a 0.2 filter. The sterile filtrate was recombined at a ratio of 1 mL filtrate, 3 mL bacterial culture, and 5 mL TSB and reincubated. This process was repeated for a total of four incubation periods. To determine final plaque forming units (PFU) of the amplified bacteriophages, 1 mL sterile filtrate was combined with 100 μL of $10^7$ CFU/mL SE and 1.5 mL TSA poured over a warm TSA petri plate (soft agar overlay plates). This experiment was repeated two times. Isolated bacteriophages were sequentially passed on soft agar overlay plates at least three times to ensure bacteriophage isolate purity.

Of the 35 bacterial isolates screened, SE selected bacteriophages were able to amplify in four different isolates (FIG. 1). In trial 1, the titer of the original 44-pooled bacteriophages was $4.1 \times 10^8$ PFU, and the estimated level of bacteriophages after passage without amplification was $1.0 \times 10^5$ PFU. Four of the tested 35 bacterial isolates (designated 8, 10, 23, and 24) amplified at least one of the bacteriophages in the original pooled culture beyond the titer of the unamplified bacteriophage culture. In trial 2, the titer of the original 44-pooled bacteriophages was $1.22 \times 10^9$ PFU, and the estimated level of bacteriophages after passage without amplification was $1.8 \times 10^5$ PFU. All 35 bacterial isolates were screened against the pooled bacteriophages. The same four bacterial isolates—8, 10, 23, and 24—amplified at least one of the bacteriophages beyond the titer of the unamplified bacteriophage culture.

To confirm amplification and lysis of the selected alternative host bacteria by the selected wide-host range bacteriophages isolated above, a second experiment was conducted in which selected bacteriophages and the alternative host bacteria were combined for co-incubation as described previously for two incubation periods. To confirm lysis of the alternative host bacteria, PFU were determined using soft agar overlay plates utilizing the alternative host bacteria.

Figure 2:
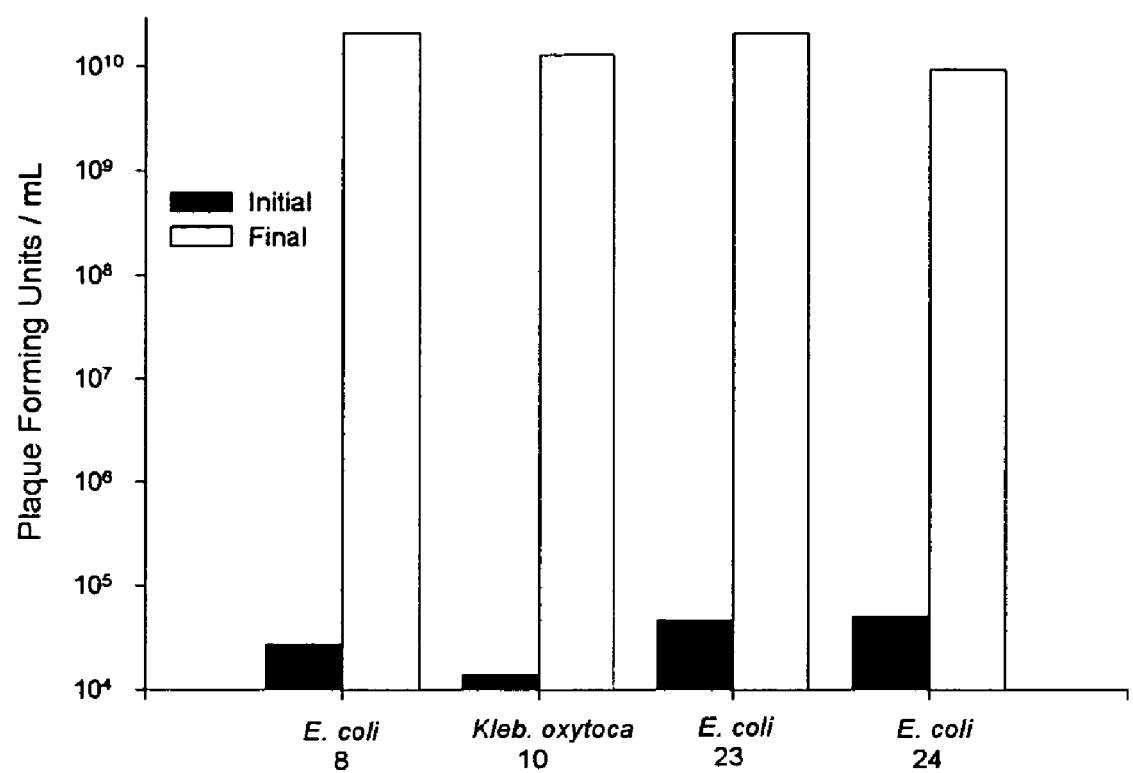
FIG. 2 is a graph showing amplification of wide-host-range bacteriophages in alternative hosts. Bacteriophages from *Salmonella enteritidis* soft agar overlay plates after enrichment in the alternative host bacteria were isolated and re-amplified in the alternative host. The bacteriophages were then plated using the soft agar overlay method on the respective alternative host bacteria.

The selected wide host range bacteriophages, numbered according to the alternative host bacteria in which they amplify, namely bacteriophage 8, 10, 23, and 24, were amplified in their respective alternative host bacteria. Initial PFU were $2.7 \times 10^4$, $1.4 \times 10^4$, $4.6 \times 10^4$ and $5.1 \times 10^4$, respectively. After two incubation periods, the final titer of the bacteriophages was determined on soft agar plates utilizing the alternative host bacteria. The final PFU of each bacteriophage were $2.8 \times 10^{10}$, $1.28 \times 10^{10}$, $2.04 \times 10^{10}$, and $9.2 \times 10^9$, respectively (FIG. 2).

Amplification of Bacteriophages in Pathogenic Bacteria.

To determine the *Salmonella* host range of the selected wide-host range bacteriophages, 10 different field isolates of *Salmonella* identified by the National Veterinary State Laboratory were utilized. The species included *S. heidelberg*, *S. montevideo*, *S. ohio*, *S. hadar*, *S. typhimurium*, *S. agona*, *S. kentucky*, *S. infantis*, *S. minnesota*, and *S. seftenberg*. For this experiment, each bacterial isolate was grown to turbidity and combined with each of the 4 selected wide-host range bacteriophages so that each bacteriophage was tested individually against 10 different *Salmonella* isolates. Bacteriophages and bacteria were combined for co-incubation as described above for two passages. PFU were determined using SE soft agar overlay plates.

Figure 3:
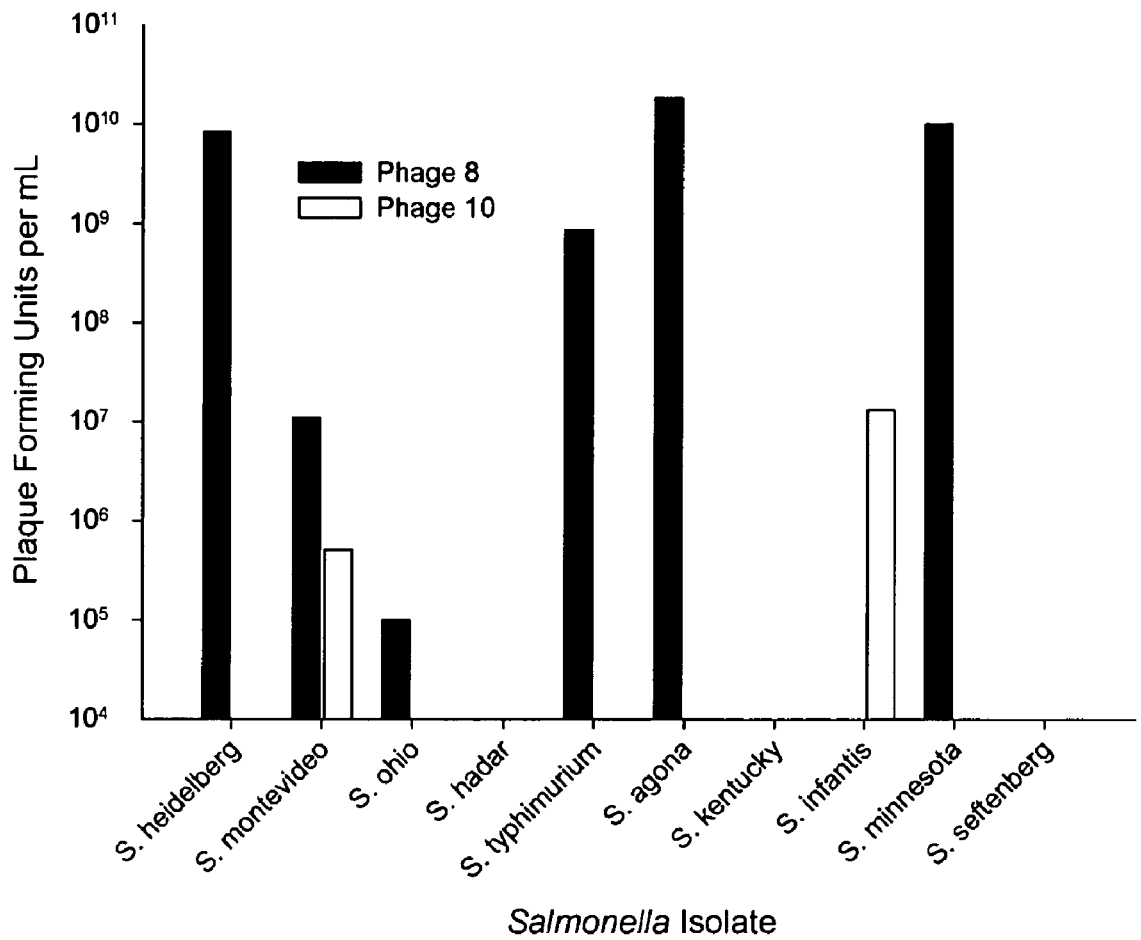
FIG. 3 is a graph showing amplification as measured by PFU/mL of two wide host range bacteriophages on 10 *Salmonella* species. Bacteriophages were individually amplified in each species of *Salmonella* and PFU determined using soft agar overlay plates.

Two of the wide-host range bacteriophages, 8 and 10, were able to amplify in different species of *Salmonella*. (FIG. 3). Bacteriophage 8 was able to amplify in six different species of *Salmonella* including *S. heidelberg, S. montevideo, S. ohio, S. typhimurium, S. agona*, and *S. minnesota*. Bacteriophage 10 was able to amplify in two additional different species of *Salmonella, S. heidelberg* and *S. infantis*. A similar experiment was performed, and one bacteriophage isolate was also able to amplify in both *E. coli* O157:H7 and SE.

Disinfection of Poultry Carcasses.

Commercially processed broiler carcasses were removed from the processing line immediately prior to chill tank immersion. Each carcass was placed in an individual carcass rinse bag (35×48 cm; VWR International, South Plainfield, N.J.), sealed with a cable tie, and randomly assigned to treatment groups. Carcasses were transported to the laboratory, and each carcass was inoculated with SE or ST according to the methods described by Cox et al. (1980) incorporated herein by reference in its entirety. Briefly, a sterile cell spreader was used to thoroughly spread 100 µL of inoculum over the entire breast area. Colony forming units of each inoculum are listed in Table 1. Each broiler carcass was then placed back into its original bag and stored at 4° C. for 2 h. Carcasses were then individually removed from each bag and sprayed with 5.5 mL of sterile saline alone (controls) or saline containing the wide host range bacteriophage (WHRφ), isolated and amplified as described above.

TABLE 1

Colony forming units (per carcass) of *Salmonella enteritidis* (SE) or *Salmonella typhimurium* (ST) used to inoculate broiler carcasses and, plaque forming units of wide-host-range bacteriophage (WHRφ) used to treat inoculated carcasses.

|  | CFU SE | CFU ST | PFU WHRφ |
|---|---|---|---|
| Experiment 1 | 40 | —* | $2.9 \times 10^9$ |
| Experiment 2 | 110 | —* | $6.0 \times 10^9$ |
| Experiment 3 | 41 | 31 | $2.1 \times 10^9$ |
| Experiment 4 | 51 | 3 | $1.7 \times 10^9$ |

*ST not added this experiment

Hand-held garden sprayers were calibrated to apply a fine mist of treatment over the breast area (5.5 mL/carcass). The PFU of WHRφ applied during each experiment is also listed in Table 1. One hundred mL of sterile water was then added to the abdominothoracic cavity of each carcass, the bag was sealed with a cable tie, and the contents were vigorously shaken by hand for 30 s. The rinse fluid was aseptically collected in sterile sealed containers and an equal volume of concentrated (2×) tetrathionate broth base was added to the rinse fluid of each sample, and samples were enriched and plated for *Salmonella* recovery as described above. Ten carcasses were used as negative controls to ensure that inoculated carcasses did not contain a field isolate of *Salmonella*. These results show that the WHRφ rinse was able to reduce concentrations of *Salmonella* to below detectable levels (Table 2).

TABLE 2

Recovery (positive/total) of *Salmonella enteritidis* (SE) or *Salmonella typhimurium* (ST) from broiler carcasses treated with spray application of 5.5 mL of wide-host-range bacteriophage (WHRφ).

|  | SE | | ST | |
|---|---|---|---|---|
|  | Control[1] | Treated | Control | Treated |
| Exp. 1[2] | 18/20 | 5/20* | —[3] | |
| Exp. 2[4] | 20/20 | 2/20* | —[3] | |
| Exp. 3[5] | 19/20 | 0/20* | 18/20 | 2/20* |
| Exp. 4[6] | 15/20 | 0/20* | 15/20 | 8/20* |

[1]all negative controls tested were negative for *Salmonella* recovery
[2]40 CFU SE, $2.9 \times 10^9$ PFU WHRφ
[3]ST not added this experiment
[4]110 CFU SE, $6 \times 10^9$ PFU WHRφ
[5]41 CFU SE, 31 CFU ST, $2.1 \times 10^9$ PFU WHRφ
[6]51 CFU SE, 3 CFU ST, $1.7 \times 10^9$ PFU WHRφ
*values are significantly different (P < 0.05) within experiments As reported in Table 2, recovery of SE was reduced from 18/20 in the control group to 5/20 in the treated group in experiment 1. The results represent a 65% reduction in recovery of SE and represented a significant reduction in SE. Experiment 2 also resulted in a significant reduction of SE, with a 90% reduction of SE recovered on treated vs. control carcasses. In experiments 3 and 4, both SE and ST were reduced significantly. No SE was detected on phage-treated carcasses for both experiments. In experiment 3, an 80% reduction of ST was seen and, a 35% reduction in recovery was noted for experiment 4. The data indicate that bacteriophages can successfully reduce the levels of SE and ST on processed broiler carcasses.

Figure 4:
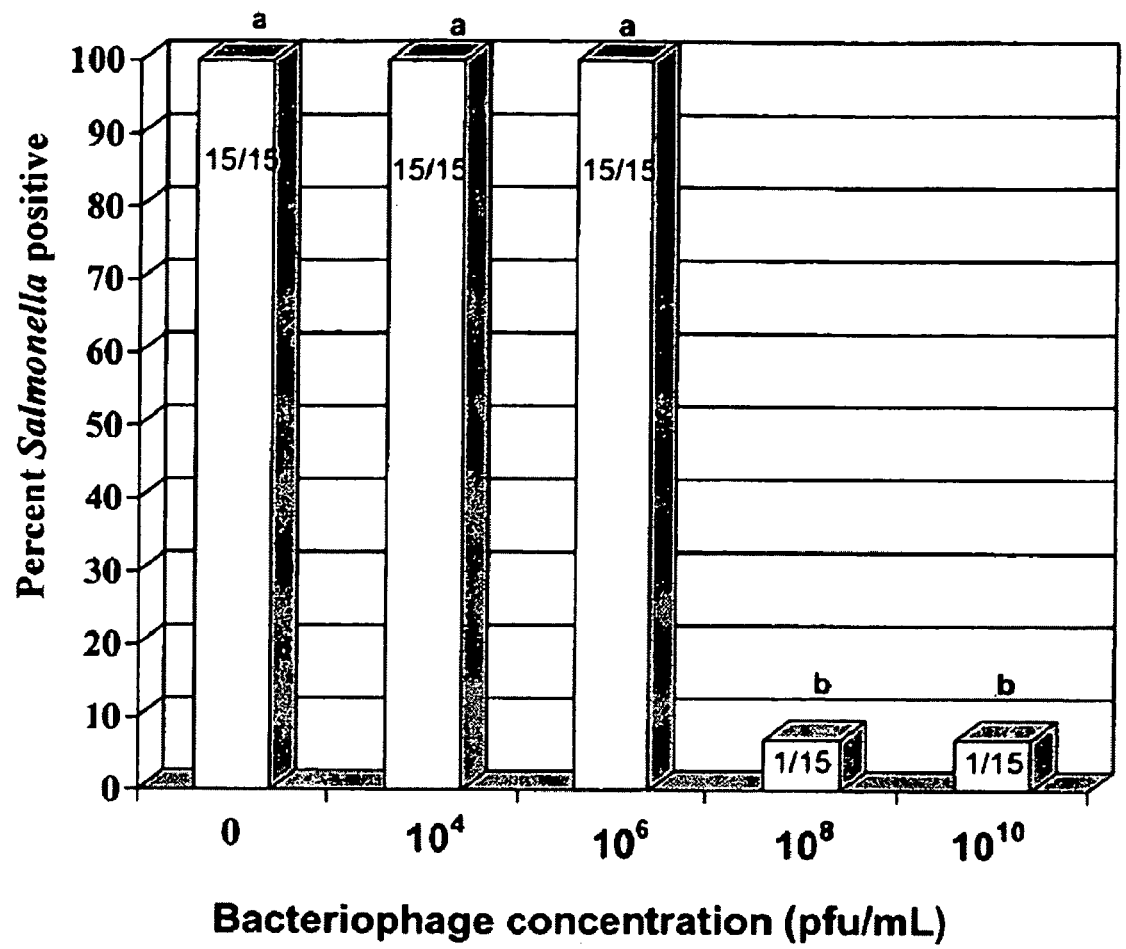
FIG. 4 is a graph showing recovery of *Salmonella enteritidis* (SE) from broiler carcasses inoculated with 20 CFU of SE, and sprayed with 5.5 mL of 0 or $0.53 \times 10^4$, $10^6$, $10^8$, or $10^{10}$ PFU/mL of a single bacteriophage isolate. Bacteriophages were amplified in alternative host bacteria prior to inoculation eliminating the risk of accidental introduction of a pathogenic bacterium to a food product. $^{a-b}$Different superscripts indicate significant (P<0.05) differences in recovery incidence.

In FIG. 4, broiler carcasses were intentionally inoculated with *Salmonella enteritidis* (SE) (20 CFU per carcass) and sprayed with 5.5 mL of sterile saline either alone (control) or containing $0.53 \times 10^4, 10^6, 10^8,$ or $10^{10}$ PFU/mL phage isolate. The broiler carcasses were placed in a bag with 100 mL sterile saline and vigorously shaken for 30 sec. The rinse fluid was collected and plated for *Salmonella* recovery. As demonstrated in FIG. 4, *Salmonella* recovery from broiler carcasses was significantly reduced by treatment with bacteriophage in a dose-dependent manner.

Figure 5:
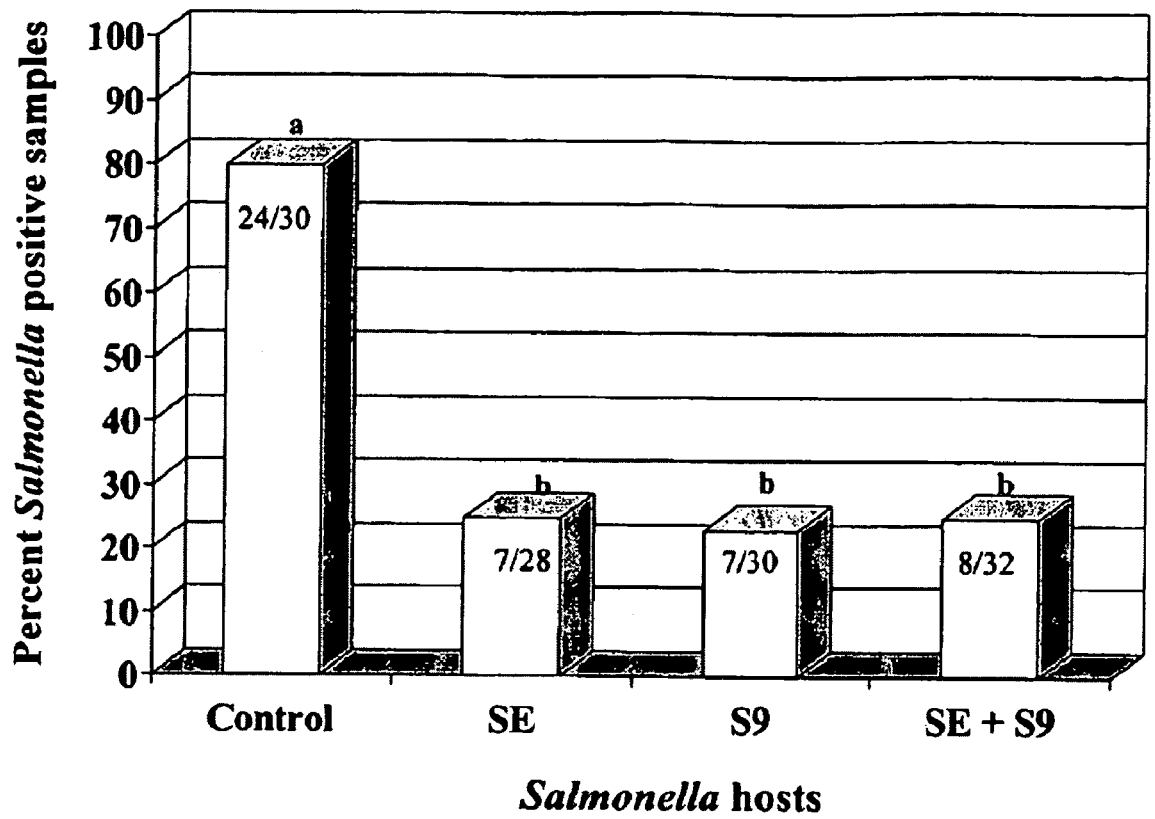
FIG. 5 is a graph showing recovery of *Salmonella* from commercial turkey carcasses rinsed with saline (control), saline containing 72 individual bacteriophage isolates amplified either in the original *Salmonella enteritidis* host (collectively $1.6 \times 10^8$ PFU/mL), in the *Salmonella* field isolate (S9) obtained from the flock antemortem ($1.8 \times 10^7$ PFU/mL) or a combination of both ($8.9 \times 10^7$ PFU/mL). $^{a-b}$Different superscripts indicate significant differences (P<0.05) in incidence between groups.

In FIG. 5, commercially processed turkey carcasses were rinsed with saline alone (control) or water containing the pooled wild-type bacteriophages isolated against SE. The pooled bacteriophages were amplified in SE, or S9 (a *Salmonella* field isolate obtained from the flock antemortem), or a combination of SE and S9. All of the bacteriophage treatments significantly reduced the frequency (p<0.05) of *Salmonella* recovery from the turkey carcasses as compared to controls.

Sensitivity of the Bacteriophages to Low pH.

Four phage isolates (PHL 4, 5, 16, and 24) were used to evaluate survival of the bacteriophage during exposure to simulated acidic conditions within the proventriculus of poultry. Sterile sample cups were filled with 50 mL of TSB, and 0.5 mL of each phage in suspension was added to two duplicate cups (eight cups total). The pH of the solution in one cup was dropped to pH 2.0 by the addition of hydrochloric acid (HCl). The pH of the duplicate cup for each phage was maintained at the pH (7.4) of the unadjusted media to serve as a control. All the cups were then incubated for 30 min at 41.5 C°. After incubation, the pH of the treated media was readjusted to 7.4 by the addition of 1M sodium hydroxide (NaOH) solution. One mL from each cup was then filtered, serially diluted, and plated using the soft agar overlay method to determine the number of PFU of phage per mL of solution.

Figure 6:
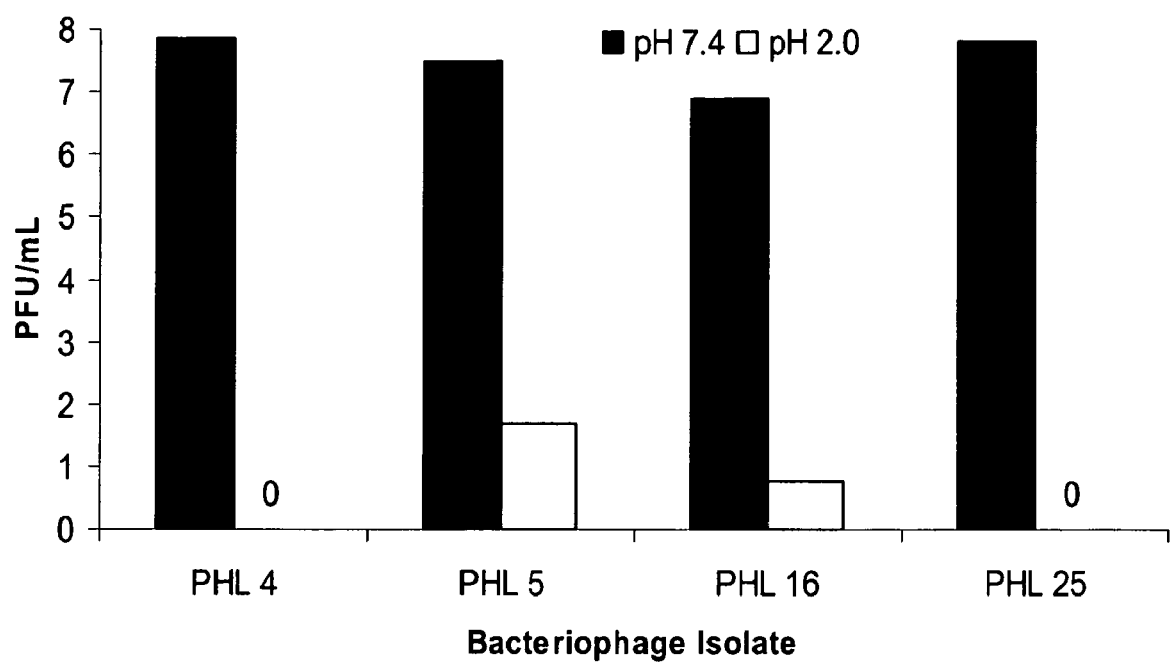
FIG. 6 is a graph showing survival of bacteriophage isolates PHL 4, 5, 16, and 24 after 30 min incubation at pH 2.0 or 7.4. Plaque forming units per mL (PFU/mL) were recovered by soft agar overlay plating. Treated media was adjusted to pH 2.0 using HCl immediately following addition of bacteriophage, and readjusted to pH 7.4 immediately following incubation for 30 min.

The pH, time and temperature were selected to simulate passage through the proventriculus of chicks, which the bacteriophage must travel through before reaching the intestinal tract or cecae. After brief incubation at pH 2.0, the numbers of bacteriophages recovered were markedly reduced (FIG. 6). However, PHL 5 and PHL 16 were able to survive the treatment conditions. Successive treatments of amplification followed by incubation in pH 2 for 30 minutes at 41.5 C° would result in increased survivability of PHL 5 and PHL 16.

Similar methods will be used to select for phages that can withstand other adverse conditions, including but not limited to, high pH, desiccation, low/high temperature and low/high pressure.

Phage Survival in the Upper GI Tract of Chicks.

The same phage isolates were evaluated for their ability to survive the environmental conditions of the upper GI tract of chicks in vivo. Each phage isolate was suspended in 1 mL of sterile saline with 1 mg of fluorescein. Twelve chicks (three chicks per phage isolate) were orally gavaged with 0.25 mL of phage and fluorescein suspension. Fifteen minutes post-treatment, chicks were humanely killed and the upper and lower ileum were briefly examined under black light. In all 12 chicks, fluorescein dye was detected in the lower ileum. The upper and lower ileum were then collected and placed in individual tubes with 5 mL of sterile saline, vortexed for 20 s, and sterile filtered using a 0.22 µm membrane. The filtrate was plated using the soft agar overlay technique to determine phage PFU per sample recovered.

From chicks gavaged with PHL 16 or PHL 24, no bacteriophages were recovered from the upper or lower ileum, and few were recovered from chicks treated with PHL 4 (Table 3). PHL 5 was best able to survive upper GI tract environmental conditions (Table 3). This is the same phage (PHL 5) that was best able to survive the low pH conditions as shown in FIG. 6. Thus, selection for low pH is a good model for selection to survive the upper GI tract.

TABLE 3

Recovery of bacteriophage isolates 4, 5, 16, and 24 from the ileum of chicks following administration of approximately $2.5 \times 10^6$ PFU by oral gavage.
Each phage isolate was suspended with fluorescein. Chicks were orally gavaged with the phage and fluorescein suspension. Fifteen minutes post-treatment, the upper and lower ileum were briefly examined under black light. In all chicks, fluorescein dye was detected in the lower ileum. The upper and lower ileum were then collected and placed in individual tubes of sterile saline, vortexed, and sterile filtered. The filtrate was plated using soft agar overlay technique to determine phage PFU per sample recovered.

|  | pfu/mL | |
| --- | --- | --- |
| Bacteriophage Isolate | Upper Ileum | Lower Ileum |
| PHL 4 | 24 | 1 |
| PHL 5 | 43 | 250 |
| PHL 16 | 0 | 0 |
| PHL 24 | 0 | 0 |

Oral Administration in an Alternative Host Bacterium.

Two wild-type phage isolates (WHR 8 and WHR 10) were selected for their ability to amplify in alternative host bacteria. Phage WHR 8 was amplified to $2 \times 10^9$ P/mL in *E. coli* and WHR 10 was amplified to $3 \times 10^9$ PFU/mL in *Klebsiella oxytoca*. Alternative host bacteria were grown in an overnight culture of tryptic soy broth. Phages were combined with their respective alternative host bacteria at a ratio of 100 mL phage: 10 mL alternative host bacteria and allowed to incubate at 37° C. for 10 min prior to administration by oral gavage. Two groups, one for each alternative host bacteria, were administered a 100× dilution of alternative host bacteria plus 1% skim milk in the drinking water. At 6 h, 26 h, and 77 h post-gavage, an intestinal sample including ceca, lower small intestine, and large intestine were aseptically removed from a portion of the chicks. Samples from 5 birds were combined in a single sample bag, and 5 sample bags were filled for titering of phage survival. Titer was determined using soft agar overlay plates with SE.

Figure 7:
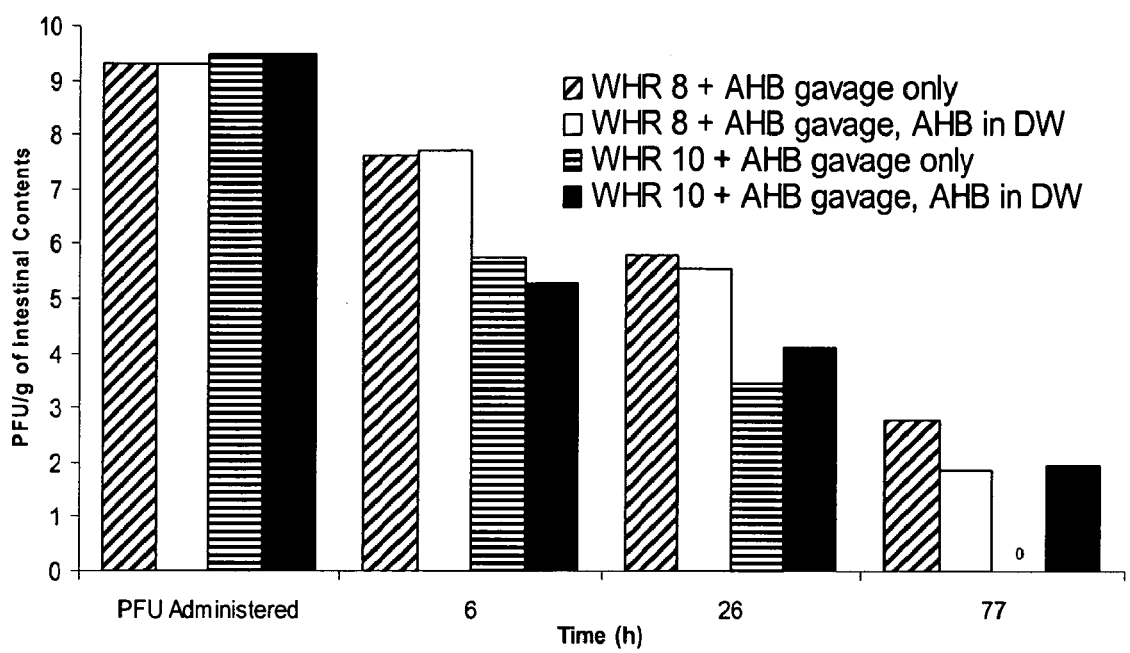
FIG. 7 is a graph showing recovery of wide host range bacteriophages (WHR) 8 and 10 from the lower gastrointestinal tract of broiler chicks. Day of hatch broilers were administered bacteriophages and alternative host bacteria (AHB) by gavage only or with the addition of AHB in the drinking water (DW). Lower ileum, cecae, and large intestine were collected 6, 26, and 77 h post-gavage. Sterile saline was added and samples were sterile filtered. PFU were determined using soft agar overlay.

While there was a reduction seen in phage recovery (FIG. 7), WHR 8 was recovered at a loss of just 1.67 log 10 at 6 h when administered by gavage alone, and a loss of only 1.59 log 10 when alternative host bacteria is added to drinking water. WHR 10 experienced greater loss of 3.73 log 10 and 4.21 log 10, respectively. These losses are less than those seen when the bacteriophages were administered directly to the chicks. (See Table 3.)

WHR 10 was evaluated at different ratios with alternative host bacteria and when administered every 12 h. Alternative host bacteria and phage were prepared as described above. In group 1, phage were administered by gavage alone. Group 2 was WHR 10+ alternative host bacteria by gavage only. Group 3 was also gavaged with WHR 10+alternative host bacteria and also had 5.35 log 10/mL in the drinking water throughout the entire experiment. Group 4 was the same as group 3, but alternative host bacteria was 6.35 log 10/mL in the DW. Phage+alternative host bacteria were administered by oral gavage every 12 h in group 5. Samples were recovered as described above. Samples were taken 6 h, 24 h, and 72 h post gavage.

Figure 8:
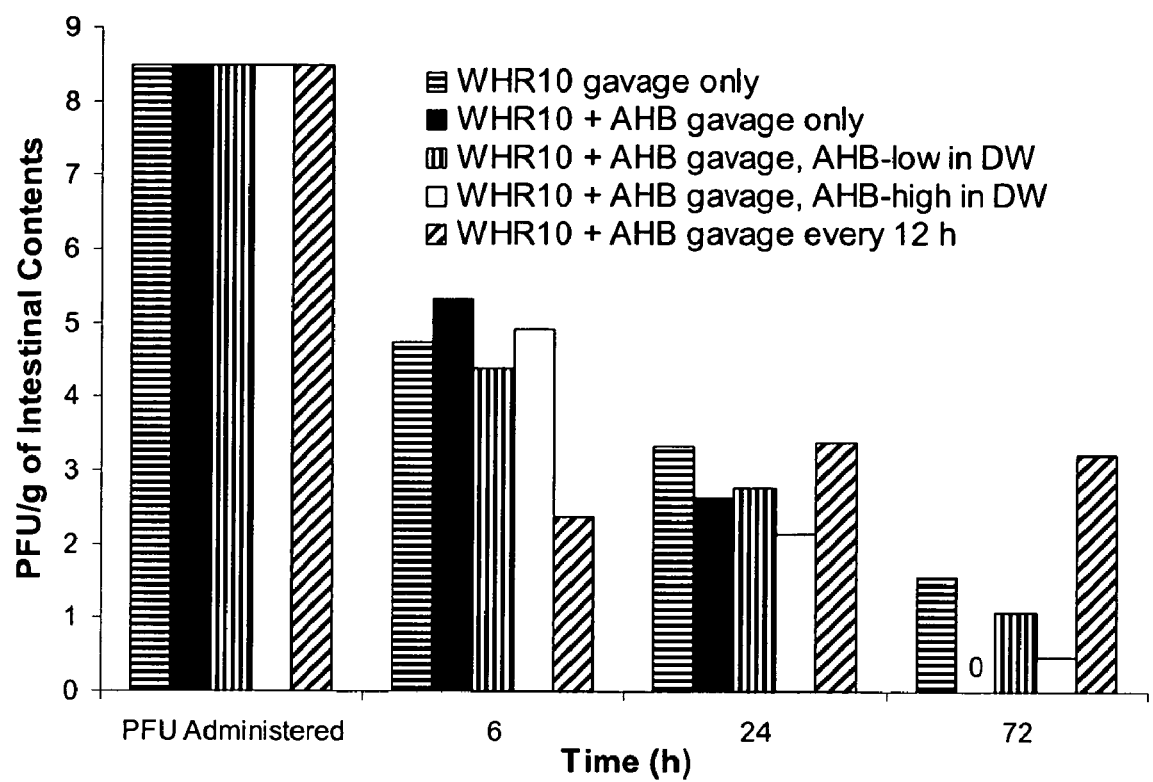
FIG. 8 is a graph showing recovery of WHR 10 from the lower gastrointestinal tract of broiler chicks. Phage was administered by oral gavage with alternative host bacteria (AHB). Treatments were gavage only, or subsequent addition of AHB at different levels in the drinking water (DW). Lower ileum, cecae, and large intestine were collected 6, 24, and 72 h post-gavage. Sterile saline was added and samples were sterile filtered. PFU were determined using soft agar overlay.

As demonstrated in FIG. 8, WHR 10 recovery dropped by 3 to 6 log 10 based on treatment method. The level of alternative host bacteria administered in the drinking water had no effect on recovery of phage from the lower GI tract, and levels of recovered PFU steadily declined throughout the experiment for groups 1-4. With the administration of phage every 12 hours, the level of recoverable phage remained constant for the full 72 h. This level is higher than any value previously recorded in the literature.

Therapeutic Treatment In Vivo.

Bacteriophages were selected for pH tolerance and ability to survive the gastrointestinal tract of chicks by passage through three chicks each time for three serial passages. Briefly, a mixture of wild-type isolates was administered to SE infected poults by oral gavage. When a feed passage marker was observed in the feces, the poults were killed, and the ileum, cecal tonsils, and cecae were removed and enriched for 30 minutes with TSB and SE. Phages isolated following the first passage were administered to the second group of poults. The process was repeated two more times. In addition, $Mg(OH)_2$ was added to the bacteriophage treatment to act as an antacid, protecting the bacteriophages from the acidic conditions of the upper GIT. Because of the buffering capabilities of $Mg(OH)_2$, perhaps more bacteriophages would be intact after passing through the proventriculus than without the aid of an antacid. The resulting mixture of bacteriophages was used to treat poults in two replicate experiments.

Our studies indicate that the selected, isolated and partially-characterized bacteriophages are capable of reducing *Salmonella* recovery from the intestine (Table 4). $Mg(OH)_2$ was also used as an antacid to help protect the bacteriophages from low-pH conditions in the GIT. Early cultures provided marked protection against *Salmonella* infection. The bacteriophages are therapeutically effective in poults. The bacteriophage isolates may also be effective against other enteric bacterial pathogens due to their wide host range (see FIG. 1).

TABLE 4

Recovery of *Salmonella enteritidis* (SE) from cecal
contents of poults challenged with $1.6 \times 10^4$ cfu
of SE 48 hours after placement, and treated with $7.5 \times 10^9$ pfu of selected bacteriophages 48 h post-challenge.

| Treatment | Average colony forming units of SE per gram cecal contents 24 h post-treatment |
|---|---|
| Control | 79,728 ± 25,893 |
| Mg(OH)$_2$ and bacteriophage | 11,224 ± 9,110 |

The beneficial bacterial cultures (alternative hosts) can also be provided continuously in the drinking water either alone or in combination with the bacteriophage after initial bacteriophage/alternative host administration. By this method, very high levels of the bacteriophages are maintained in the gastrointestinal tract. Experiments have proven remarkably effective at protecting young poultry from a *Salmonella enteritidis* enteric infection. In these studies, large numbers of bacteriophages were isolated from the ceca of birds treated with a combination of the alternative host bacterial culture and bacteriophages. Table 5 shows that when bacteriophage is added in gavage and/or water the recovery of SE is zero.

TABLE 5

Effect of Combination Treatment of Bacteriophage (Ø) and
a Beneficial Bacterial Culture Serving as an Alternative Bacteriophage
Host (Mean cfu of SE/g cecal contents in log$_{10}$ units)

| Group | Treatment | 24 h | 48 h | 72 h |
|---|---|---|---|---|
| 1 | Control Challenged with SE day 1 | 6.02 ± 5.40 | 5.53 ± 5.15 | 4.78 ± 4.30 |
| 2 | Prophylactic Ø + FN gavage FN in H$_2$O | 0 | 0 | 0 |
| 3 | Prophylactic Ø + FN gavage Ø + FN in water | 0 | 0 | 0 |

Disinfection of Surfaces.

In order to use WHR bacteriophages to sanitize against disease-causing bacteria, the phages must be able to survive drying to have a lasting effect on any bacteria introduced after the phages are applied. We will progressively select for such phages. As an example of a contaminated surface, we will disassemble a keyboard and use individual keypads to test previously selected bacteriophages. The phage will be pooled to maintain the simplicity of the experiment.

Eleven individual keypads will be immersed in the pooled phages for approximately 10 seconds. The keypads will then be placed on a metal drying rack in a laminar flow hood to prevent contamination. One keypad will not be allowed to dry, and will be used to determine the titer of phages that attach to the keypad. After complete drying of the keypads (1-3 hours), they will be immersed in brain heart infusion broth (BHI), and shaken vigorously to remove the phages from the keypad. The BHI will then be used to pour soft agar plates with *Staphylococcus aureus*. Any plaques on the soft agar plates will be the result of a bacteriophage that survived the drying process. The surviving bacteriophages will be amplified using *Staphylococcus aureus*, and marked as those that can withstand dry conditions upon storage.

These "dry" bacteriophages will then be subjected to the same process to increase the amounts of phages than can survive on the dry keypads. We predict that as we pass the "dry" bacteriophages through the selection process, greater and greater levels of phages will be isolated off of the dried keypads. Once we achieve a plateau of survivability, meaning that additional passes do not result in more phages, the selection process will be complete. We will then proceed to determine how many phages are necessary to kill *Staphylococcus aureus* on keypads.

Phage Biosensor.

A biosensor system will be designed to determine the viability of bacteria by their susceptibility to bacteriophage infection. Briefly, a nucleocapsid encoding the green fluorescent protein (GFP) will be incorporated into a WHRφ genome such that if the phage successfully infects a living bacterium, GFP will be expressed and can be detected. The idea is to fuse GFP with one of the capsid proteins. In brief, the phage DNA will be prepared, and a pair of primers will be designed to amplify the capsid protein gene, which is selected to be fused with the GFP gene, from the phage DNA using PCR. The amplified DNA fragments will be purified and cloned into pUC plasmid through two appropriate restriction enzymes. The rest of the phage DNA genome sequences will be amplified using high fidelity PCR enzyme such as ultra PFU enzyme from Stratagen to ensure that no mutation will be introduced in the PCR reaction. The amplified phage genomic fragments will be linked to two sides of the GFP-capsid gene based on their original orientation in the phage genome. The resultant plasmid will be introduced into *E. coli* by electroporation for production of phage. The expression of GFP phage will be confirmed using inverted fluorescence microscope (Olympus Ix-71) with ×100 oil objective and GFP-optimized filter set. The supernatant containing the phage will be passed through 0.2 μm to remove debris. The purified phage particles will be stored at −20° C. until use. The phage produced in this round will be added to the *E. coli* O157:H7 to determine the infectivity of the engineered GFP phage by phage titering approach. The infectivity of the GFP phage will be compared with original phage to determine whether the genomic modification impair the integrity of the phage. Upon the verification, we will use this GFP phage for subsequent experiments. Because a phage will only amplify in living host bacteria, the GFP modified phage will only produce GFP in the presence of viable bacteria and can be incorporated into any biosensor system as a method to determine viability.

Various features are set forth in the following claims.

We claim:

1. A composition comprising at least one isolated wild-type wide host range bacteriophage prepared by passage in a non-pathogenic, enteric bacterial isolates, wherein the wide host range bacteriophage is capable of infecting more than one genus of bacteria.

2. The composition of claim 1, wherein the composition further comprises a plurality of wide host range bacteriophages.

3. The composition of claim 1, wherein the composition further comprises a base.

4. The composition of claim 3, wherein the base is Mg(OH)$_2$.

5. The composition of claim 1, wherein the composition further comprises a non-pathogenic bacterium in which the bacteriophage is capable of replicating.

6. A method of treating a subject infected with a bacterium comprising administering the composition of claim 1 to the subject, wherein the bacteriophage is capable of lysing the bacterium to treat the infection.

7. The method of claim 6, wherein the composition is administered by ingestion or gavage.

8. The method of claim 6, wherein the composition is ingested in a food or a liquid.

9. The method of claim 6, wherein the bacteriophage comprises a plurality of wide host range bacteriophages.

10. The method of claim 6, wherein the subject is selected from the group consisting of a domestic animal, a poultry, a human and a fish.

11. The method of claim 6, wherein the infection is an enteric infection.

12. The method of claim 6, wherein the bacterium is selected from the group consisting of *Salmonella, Escherichia*, and *Klebsiella* species.

13. The method of claim 6, wherein the composition further comprises a base.

14. The method of claim 13, wherein the base is $Mg(OH)_2$.

15. The method of claim 6, wherein the composition further comprises a non-pathogenic bacterium in which the bacteriophage is capable of replicating.

16. The composition of claim 5, wherein the non-pathogenic bacterium is selected from the group consisting of *Salmonella, Escherichia*, and *Klebsiella* species.

17. The composition of claim 1, further comprising a food source.

18. The composition of claim 1, wherein the bacteriophage is capable of lysing at least one of *Salmonella, Escherichia*, and *Klebsiella* species.

* * * * *